(12) United States Patent
Sawabe et al.

(10) Patent No.: US 7,553,989 B2
(45) Date of Patent: Jun. 30, 2009

(54) MALONIC ACID MONOESTERS AND PROCESS FOR PRODUCING THE SAME

(75) Inventors: Takehiko Sawabe, Kanagawa-Ken (JP); Kazuhiro Aihara, Kanagawa-Ken (JP); Kunio Atsumi, Kanagawa-Ken (JP); Keiichi Ajito, Kanagawa-Ken (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 568 days.

(21) Appl. No.: 10/531,382

(22) PCT Filed: Oct. 17, 2003

(86) PCT No.: PCT/JP03/13319

§ 371 (c)(1), (2), (4) Date: Apr. 15, 2005

(87) PCT Pub. No.: WO2004/035540

PCT Pub. Date: Apr. 29, 2004

(65) Prior Publication Data

US 2005/0272950 A1    Dec. 8, 2005

(30) Foreign Application Priority Data

Oct. 18, 2002  (JP) ............................ 2002-304630
Feb. 27, 2003  (JP) ............................ 2003-050293

(51) Int. Cl.
  *C07C 69/34*    (2006.01)
(52) U.S. Cl. ...................... 560/190; 560/192
(58) Field of Classification Search ............... None
  See application file for complete search history.

(56) References Cited

U.S. PATENT DOCUMENTS 4,262,009 A    4/1981    Christensen et al. ........ 424/274
4,262,011 A    4/1981    Christensen et al. ........ 424/274

FOREIGN PATENT DOCUMENTS

| EP | 0632039 | 1/1995 |
|----|---------|--------|
| JP | 56-123985 | 9/1981 |
| JP | 63-255280 | 10/1988 |
| JP | 63-284176 | 11/1988 |
| JP | 08-325526 | * 10/1996 |
| JP | 08-325526 | 12/1996 |
| JP | 2666118 | 6/1997 |

OTHER PUBLICATIONS

Liebich et al, Journal of Chromatography B: Biomedical Sciences and Applications, Urinary Organic Acid Screening by Solid-phase Microextraction of the Methyl Esters, 1998, 713(2), pp. 427-432.*

* cited by examiner

*Primary Examiner*—Paul A Zucker
(74) *Attorney, Agent, or Firm*—Wenderoth, Lind & Ponack, LLP.

(57) ABSTRACT

The present invention relates to a compound represented by formula (1) or a salt thereof:

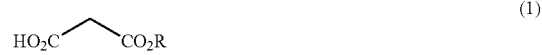

(1)

wherein R represents a group that is easily removable upon hydrolysis in vivo. This compound is usable in the production of prodrug-type carbapenem antibacterial agents for oral administration. The use of this compound in the process of production of the antibacterial agents can realize enhanced production efficiency and reduced production cost.

2 Claims, No Drawings

MALONIC ACID MONOESTERS AND PROCESS FOR PRODUCING THE SAME

This application is a 371 of PCT/JP03/13319 filed Oct. 17, 2003 which is hereby incorporated by reference in its entirety.

BACKGROUND OF THE INVENTION

1. Field of the Invention

The present invention relates to a monoester of malonic acid and a process for producing the same.

2. Related Art

Carbapenem antibacterial agents have potent antibacterial activity against a wide spectrum of Gram-positive bacteria and Gram-negative bacteria. Up to now, for example, Imipenem, Meropenem, and Biapenem have been developed as carbapenem antibacterial agents for clinical administration as injections. For example, when a strain on patients is taken into consideration, however, oral carbapenem antibacterial agents are clinically highly useful because they can be simply and easily administered and administration at home is possible. For this reason, several orally administrable carbapenem antibacterial agents have hitherto been examined (for example, Japanese Patent Publication No. 2666118).

Monoesters of malonic acid are promising compounds which can be intermediates important to the production of a number of orally administrable carbapenem antibacterial agents (for example, Japanese Patent Laid-Open Publication Nos. 123985/1981, 255280/1988, and 284176/1988).

However, it should be noted that an ester group as a protective group of a carboxyl group in the monoester of malonic acid used in the conventional production process of carbapenem antibacterial agents is a substituent that cannot easily be removed by hydrolysis in vivo (for example, a p-nitrobenzyl ester group). In the prior art technique, a contemplated prodrug-type carbapenem antibacterial agent for oral administration is produced by converting the monoester of malonic acid with this protective group to a predetermined intermediate, then removing the ester group as the protective group derived from the monoester of malonic acid (deprotection step), and further converting that part to an ester group that can easily be hydrolyzed in vivo (prodrug preparation step).

As far as the present inventors know, up to now, the use of a group, which can easily be hydrolyzed and removed in vivo, as an ester group which is the protective group of the carboxyl group in the monoester of malonic acid used in the production process of carbapenem antibacterial agents has not been known. Further, specific compounds of the monoester of malonic acid with the above ester group, and the production process and property data of such compounds have not hitherto been disclosed.

SUMMARY OF THE INVENTION

The present inventors have now unexpectedly found that a monoester of malonic acid containing a group which can easily be removed upon hydrolysis in vivo can be selectively produced from malonic acid in one step and that the use of this monoester of malonic acid in the production of carbapenem antibacterial agents for oral administration can realize the production of prodrug-type carbapenem antibacterial agents for oral administration in a process shorter than the conventional process with a higher efficiency at a lower cost. The present invention has been made based on such finding.

Accordingly, an object of the present invention is to provide a monoester of malonic acid containing a group, which can easily be removed upon hydrolysis in vivo, and usable in the production of prodrug-type carbapenem antibacterial agents for oral administration, and a process for producing said monoester of malonic acid.

According to one aspect of the present invention, there is provided a compound represented by formula (1) or a salt thereof:

(1)

wherein R represents a group that is easily removable upon hydrolysis in vivo.

According to another aspect of the present invention, there is provided a process for producing a compound represented by formula (1) or a salt thereof, said process comprising the step of reacting malonic acid with a compound represented by formula (2) in the presence of a base:

(2)

wherein
R represents a group that, in the form of an ester —COOR, can be degraded and is easily removable in vivo; and
X represents a halogen atom.

According to a further aspect of the present invention, there is provided a process for producing a prodrug-type medicinal compound containing an ester group —COOR, said process comprising the step of introducing a —COOR group into a precursor compound of said compound using a compound represented by formula (1) or a salt thereof. In this case, R represents a group that is easily removable upon hydrolysis in vivo.

The use of the monoester of malonic acid according to the present invention can realize the elimination of two steps, i.e., a deprotection step and a prodrug preparation step, from the conventional production process of a carbapenem antibacterial agent for oral administration. This can contribute to increased efficiency of the production process of the carbapenem antibacterial agent for oral administration, and reduced production cost.

DETAILED DESCRIPTION OF THE INVENTION

Compound of Formula (1)

The term "C1-C6 alkyl" or "C1-C6 alkoxy" as used herein as a group or a part of a group means straight chain or branched chain alkyl or alkoxy having 1 to 6 carbon atoms.

"C1-C6 alkyl" is preferably C1-C5 alkyl, more preferably C1-C4 alkyl, still more preferably C1-C3 alkyl, even more preferably C1-C2 alkyl.

Examples of alkyl include straight chain alkyls such as methyl, ethyl, propyl, butyl, pentyl, hexyl, and heptyl and branched chain alkyls such as isopropyl, isobutyl, s-butyl, t-butyl, neopentyl, isopentyl, and isohexyl.

"C1-C6 alkoxy" is preferably C1-C5 alkoxy, more preferably C1-C4 alkoxy, still more preferably C1-C3 alkoxy, even more preferably C1-C2 alkoxy.

Examples of alkoxy include methoxy, ethoxy, n-propoxy, i-propoxy, n-butoxy, i-butoxy, s-butoxy, and t-butoxy.

The term "C3-C8 cycloalkyl" as used herein as a group or a part of a group means monocyclic alkyl having 3 to 8 carbon atoms.

"C3-C8 cycloalkyl" is preferably C3-C6 cycloalkyl, more preferably C4-C6 cycloalkyl, still more preferably C5-C6 cycloalkyl, particularly preferably cyclohexyl.

Examples of cycloalkyl include cyclopropyl, cyclobutyl, cyclopentyl, and cyclohexyl.

The term "C2-C6 alkenyl" or "C2-C6 alkynyl" as used herein as a group or a part of a group means straight chain or branched chain alkenyl or alkynyl having 2 to 6 carbon atoms.

"C2-C6 alkenyl" is preferably C2-C5 alkenyl, more preferably C2-C4 alkenyl.

Examples of alkenyl include vinyl, allyl, propenyl, isopropenyl, butenyl, 2-butenyl, 3-butenyl, 2-methyl-1-propenyl, 2-methylallyl, pentenyl, 2-pentenyl, cyclopentenyl, hexenyl, and 2-hexenyl.

"C2-C6 alkynyl" is preferably C2-C5 alkynyl, more preferably C2-C4 alkynyl.

Examples of alkynyl include ethynyl, propynyl, 2-propynyl, butynyl, 2-butynyl, 3-butynyl, pentynyl, 2-pentynyl, 3-pentynyl, 4-pentynyl, hexynyl, 2-hexynyl, 3-hexynyl, 4-hexynyl, and 5-hexynyl.

The term "aryl" as used herein as a group or a part of a group means phenyl or naphthyl.

The term "five- to seven-membered heterocyclic group" as used herein means a five- to seven-membered (preferably five- or six-membered) monocyclic saturated or unsaturated heterocyclic group. That is, in the five- to seven-membered heterocyclic group, one to four of the ring atoms may be hetero-atoms with the remaining ring atoms being carbon atoms. The hetero-atom may be selected from oxygen, nitrogen, and sulfur atoms.

Examples of "five- to seven-membered heterocyclic group" include furan, pyrrole, imidazole, thiazole, triazole, thiadiazole, pyridine, pyridazine, pyrimidine, and pyrazine.

The term "halogen atom" as used herein means a fluorine, chlorine, bromine, or iodine atom.

In formula (1), R represents a group which can easily be removed upon hydrolysis in vivo. The expression "group which is easily removable upon hydrolysis in vivo" (group R) as used herein refers to a group that, when a compound containing the group in the form of an ester group —CO$_2$R is incorporated into an organism, the ester group is easily degraded by hydrolysis and removed from the compound as a result of an in-vivo enzymatic or in-vivo chemical reaction. Group R is not particularly limited so far as it has such properties. For example, in the field of β-lactam antibacterial agents, when R in the form of an ester group —CO$_2$R is introduced into a target antibacterial agent compound, a prodrug capable of promoting oral absorption is produced. Upon uptake of the prodrug into an organism, R is removed from the ester group part, and, consequently, the prodrug is converted to an antibacterial agent compound having excellent antibacterial activity.

In the present invention, preferably, R represents (a) C1-C6 alkylcarbonyloxy C1-C6 alkyl,
(b) arylcarbonyloxy C1-C6 alkyl,
(c) five- to seven-membered heterocyclic carbonyloxy C1-C6 alkyl,
(d) C2-C6 alkenylcarbonyloxy C1-C6 alkyl,
(e) C2-C6 alkynylcarbonyloxy C1-C6 alkyl,
(f) C3-C8 cycloalkylcarbonyloxy C1-C6 alkyl,
(g) C1-C6 alkoxycarbonyloxy C1-C6 alkyl,
(h) aryloxycarbonyloxy C1-C6 alkyl,
(i) five- to seven-membered heterocyclic oxycarbonyloxy C1-C6 alkyl,
(j) C2-C6 alkenyloxycarbonyloxy C1-C6 alkyl,
(k) C2-C6 alkynyloxycarbonyloxy C1-C6 alkyl,
(l) C3-C8 cycloalkyloxycarbonyloxy C1-C6 alkyl,
(m) phthalid-3-yl, or
(n) 2-oxo-5-(C1-C6 alkyl)-1,3-dioxolen-4-ylmethyl.

In this case, groups (a) to (n) are optionally substituted by a substituent selected from the group consisting of:

C1-C6 alkyl; C3-C8 cycloalkyl; C1-C6 alkoxy; C2-C6 alkenyl; C2-C6 alkynyl; aryl optionally substituted by C1-C6 alkyl; five- to seven-membered heterocyclic group; C1-C6 alkylcarbonyloxy; C1-C6 alkoxycarbonyloxy; arylcarbonyloxy; aryloxycarbonyloxy; C1-C6 alkylthio; C2-C6 alkenylthio; and di-C1-C6 alkylamino.

In this case, that groups (a) to (n) "are optionally substituted by" a substituent means that one or more hydrogen atoms on groups (a) to (n) are optionally substituted by one or more substituents (which may be the same or different), or groups (a) to (n) may be unsubstituted groups which are not substituted by any substituent. It would be apparent to a person having ordinary skill in the art that, when groups (a) to (n) are substituted, the maximum number of substituents on groups (a) to (n) may be determined depending upon the number of substitutable hydrogen atoms on the alkyl.

For example, p-methylphenyl may be mentioned as the "aryl optionally substituted by C1-C6 alkyl."

Preferably, the substituent in R is selected from the group consisting of C1-C6 alkyl, C3-C8 cycloalkyl, C1-C6 alkoxy, C2-C6 alkenyl, C2-C6 alkynyl, aryl, and five- to seven-membered heterocyclic group.

More preferably, the substituent in R is C1-C4 alkyl or C3-C6 cycloalkyl.

In groups (a) to (n), aryl refers to phenyl or naphthyl.

In a more preferred embodiment of the present invention, R is selected from groups (a), (b), (d), (f) to (h), (j), and (l) to (n). These groups may be substituted by the above substituent.

In a further preferred embodiment of the present invention, R represents (a') C1-C6 alkylcarbonyloxy C1-C6 alkyl optionally substituted by C3-C8 cycloalkyl; or by aryl optionally substituted by C1-C6 alkyl, (b') arylcarbonyloxy C1-C6 alkyl in which the aryl part is optionally substituted by C1-C6 alkyl, (d') unsubstituted C2-C6 alkenylcarbonyloxy C1-C6 alkyl, (f') unsubstituted C3-C8 cycloalkylcarbonyloxy C1-C6 alkyl, (g') C1-C6 alkoxycarbonyloxy C1-C6 alkyl optionally substituted by C3-C8 cycloalkyl; or by aryl optionally substituted by C1-C6 alkyl, (h') aryloxycarbonyloxy C1-C6 alkyl in which the aryl part is optionally substituted by C1-C6 alkyl, (j') unsubstituted C2-C6 alkenyloxycarbonyloxy C1-C6 alkyl, (l') unsubstituted C3-C8 cycloalkyloxycarbonyloxy C1-C6 alkyl, (m') unsubstituted phthalid-3-yl, or (n') unsubstituted 2-oxo-5-(C1-C6 alkyl)-1,3-dioxolen-4-ylmethyl.

In a still more preferred embodiment of the present invention, R represents (a") C1-C6 alkylcarbonyloxy C1-C2 alkyl optionally substituted by cyclohexyl, (b") phenylcarbonyloxy C1-C2 alkyl in which the phenyl part is optionally substituted by C1-C4 alkyl, (g") C1-C6 alkoxycarbonyloxy C1-C2 alkyl optionally substituted by cyclohexyl, (h") phenyloxycarbonyloxy C1-C2 alkyl in which the phenyl part is optionally substituted by C1-C4 alkyl, (l") unsubstituted C3-C6 cycloalkyloxycarbonyloxy C1-C2 alkyl, or (n") unsubstituted 2-oxo-5-(C1-C4 alkyl)-1,3-dioxolen-4-ylmethyl.

In a particularly preferred embodiment of the present invention, R is selected from the group consisting of
acetyloxymethyl,
pivaloyloxymethyl,
2,4-dimethylbenzoyloxymethyl,
1-(ethoxycarbonyloxy)ethyl,
1-(isopropoxycarbonyloxy)ethyl,
cyclohexyloxycarbonyloxymethyl,
1-(cyclohexyloxycarbonyloxy)ethyl,
1-(phenoxycarbonyloxy)ethyl,
2-oxo-5-methyl-1,3-dioxolen-4-ylmethyl,
1-(2,2-dimethylpropoxycarbonyloxy)ethyl,
1-(2-cyclohexylethoxycarbonyloxy)ethyl,
1-(isobutoxycarbonyloxy)ethyl,
isopropoxycarbonyloxymethyl,
isopentoxycarbonyloxymethyl,
isobutylcarbonyloxymethyl, and
1-ethylpropylcarbonyloxymethyl.

Accordingly, specific examples of suitable compounds represented by formula (1) according to the present invention include
monoacetyloxymethyl malonate,
monopivaloyloxymethyl malonate,
mono-2,4-dimethylbenzoyloxymethyl malonate,
mono-1-(ethoxycarbonyloxy)ethyl malonate,
mono-1-(isopropoxycarbonyloxy)ethyl malonate,
monocyclohexyloxycarbonyloxymethyl malonate,
mono-1-(cyclohexyloxycarbonyloxy)ethyl malonate,
mono-1-(phenoxycarbonyloxy)ethyl malonate,
mono-2-oxo-5-methyl-1,3-dioxolen-4-ylmethyl malonate,
mono-1-(2,2-dimethylpropoxycarbonyloxy)ethyl malonate,
mono-1-(2-cyclohexylethoxycarbonyloxy)ethyl malonate,
mono-1-(isobutoxycarbonyloxy)ethyl malonate,
monoisopropoxycarbonyloxymethyl malonate,
monoisopentoxycarbonyloxymethyl malonate,
monoisobutylcarbonyloxymethyl malonate, and
mono-1-ethylpropylcarbonyloxymethyl malonate.

Additional specific examples of compounds represented by formula (1) according to the present invention include
mono-1-(acetyloxy)ethyl malonate,
4-hexenyloxycarbonyloxymethyl malonate, and
monophthalid-3-yl malonate.

Salts of compounds represented by formula (1) include, for example, alkali metal salts such as lithium salt, sodium salt, and potassium salt; alkaline earth metal salts such as magnesium salt and calcium salt; and quaternary ammonium salts such as ammonium salt, and tetra-n-butylammonium salt.

Production of Compounds of Formula (1)

Compounds of formula (1) or salts thereof according to the present invention may be produced by a process comprising the step of reacting malonic acid with a compound represented by formula (2) in the presence of a base:

$$RX \qquad (2)$$

wherein
R represents a group that, in the form of an ester group —COOR, can be degraded and is easily removable in vivo; and
X represents a halogen atom.

In formula (2), X preferably represents a chlorine, bromine, or iodine atom, particularly preferably an iodine atom.

The starting material necessary for the synthesis of the compounds according to the present invention are commercially available or can easily be produced by a conventional method.

In the compound of formula (2), when X represents a chlorine atom, X in formula (2) can be replaced by an iodine atom by reacting the compound of formula (2) with an equivalent or slightly excessive amount of sodium iodide. This compound is suitable for use in the production process according to the present invention.

The base is generally a basic organic compound.

In the present invention, preferred bases include organic amine compounds (for example, di-lower alkylamine, tri-lower alkylamine, N-lower alkylpyrrolidine, N-lower alkylpiperidine, N-lower alkylmorpholine, and N,N-di-lower alkylaniline), and basic nitrogn-containing heterocyclic compounds (for example, lutidine, picoline, and collidine).

In a more preferred embodiment of the present invention, the base is triethylamine, N,N-diisopropylethylamine, or 2,6-lutidine.

The amount of the base used is generally 0.2 to 1.0 molar equivalent, preferably 0.2 to 0.35 molar equivalent, based on malonic acid.

The amount of the compound of formula (2) used is preferably 0.2 to 0.35 molar equivalent based on malonic acid.

The reaction in the production process of the compound of formula (1) according to the present invention is preferably carried out in an aprotic polar solvent in the presence of a base.

Any aprotic polar solvent may be used so far as it does not adversely affect the above reaction. Preferably, the aprotic polar solvent is selected from acetone, chloroform, acetonitrile, tetrahydrofuran, and dichloromethane. More preferably, the aprotic polar solvent is tetrahydrofuran or acetonitrile.

Regarding the reaction temperature, the reaction can proceed at room temperature or under heated conditions. Preferably, the reaction temperature is room temperature to 50° C. When the temperature is in the above-defined temperature range, the reaction can proceed smoothly.

In a more preferred embodiment of the present invention, in the production process of the compound of formula (1), in addition to malonic acid and the compound of formula (2), a compound of formula (3) may further be added in the reaction:

$$R^1R^2R^3R^4N^+X^- \qquad (3)$$

wherein
X$^-$ represents a halide ion; and
R$^1$ to R$^4$, which may be the same or different, represent
C1-C6 alkyl which may combine with any of R$^1$ to R$^4$ to form a ring,
aryl optionally substituted by C1-C6 alkyl,
aryl C1-C6 alkyl in which the aryl part is optionally substituted by C1-C6 alkyl,
C3-C8 cycloalkyl C1-C6 alkyl,
C3-C8 cycloalkyl,
C2-C6 alkenyl, or
C2-C6 alkynyl.

In the above reaction, when the reaction is allowed to proceed in such a state that the reaction system further contains the compound of formula (3), the compound of formula (1) can be produced in a shorter reaction time as compared with the case where the compound of formula (3) is not added.

The compound of formula (3) is commercially available or can easily be produced by a conventional method.

Ions represented by X$^-$ include fluoride ions, chloride ions, bromide ions, and iodide ions, preferably chloride ions, bromide ions, and iodide ions.

In formula (3), three- to nine-membered azacycloalkanes may be mentioned as the "C1-C6 alkyl which may combine with any of $R^1$ to $R^4$ to form a ring."

Preferably, $R^1$ to $R^4$ represent C1-C6 alkyl which may combine with any of $R^1$ to $R^4$ to form a ring; or aryl C1-C6 alkyl in which the aryl part is optionally substituted by C1-C6 alkyl.

Specific examples of compounds of formula (3) include tetra-n-butylammonium chloride, N,N-diethylpiperidinium chloride, and benzyltriethylammonium chloride. Preferably, the compound of formula (3) is benzyltriethylammonium chloride.

When the compound of formula (3) is used, the amount of the compound of formula (3) used is 0.5 to 1.5 molar equivalent, preferably 0.9 to 1.2 molar equivalent, based on the compound of formula (2).

Use of Compounds of Formula (1)

Compounds of formula (1) according to the present invention can be used as an intermediate compound for introducing —COOR in the process of synthesis of a prodrug compound having —COOR as a substituent.

According to the present invention, in a relatively early stage of the production process of a contemplated compound, —COOR can be introduced in the structure of the compound. In the course of the production process, the introduced —COOR can function also as a protective group of the carboxyl group. Further, after synthesis as the prodrug compound, —COOR functions as a prodrug ester group which, upon uptake of the prodrug compound into the organism, can easily be hydrolyzed in the organism. Therefore, when the compound according to the present invention is used in a prodrug compound synthesis process, the compound deprotection step and the prodrug preparation step required in the conventional production process can be omitted and, thus, the prodrug compound can be produced with a higher efficiency at a lower cost.

Thus, according to the present invention, there is provided a process for producing a prodrug compound having an ester group —COOR as at least one of substituents, said process comprising the step of introducing a —COOR group into a precursor compound of said prodrug compound using a compound represented by formula (1) or a salt thereof. In this case, R represents a group that is easily removable upon hydrolysis in vivo.

In a preferred embodiment of the present invention, in the production process of a prodrug compound, the —COOR group is introduced into the precursor compound by reacting a magnesium malonate represented by formula (4)

$$Mg(O_2CCH_2CO_2R)_2 \qquad (4)$$

wherein R represents a group that is easily removable upon hydrolysis in vivo, obtained by reacting the compound represented by formula (1) or a salt thereof with a magnesium salt in an organic solvent with the precursor compound of said prodrug compound.

Magnesium salts usable herein include, for example, magnesium halides such as magnesium chloride, magnesium bromide, magnesium iodide, and magnesium fluoride; complexes of magnesium halides with ether organic compounds, such as magnesium bromide-diethyl ether complex; and lower alkoxy compounds (for example, C1-C4 alkoxy compounds) of magnesium such as magnesium ethoxide and magnesium methoxide. The magnesium salt is preferably magnesium chloride or a magnesium bromide-diethyl ether complex, more preferably magnesium chloride.

Organic solvents usable herein include, for example, hydrocarbon solvents such as toluene, xylene, and cyclohexane; ether solvents such as tetrahydrofuran, dioxane, and 1,2-dimethoxyethane; halogenated hydrocarbon solvents such as methylene chloride, chloroform, and 1,2-dichloroethane; ester solvents such as methyl acetate, ethyl acetate, propyl acetate, and butyl acetate; and highly polar aprotic solvents such as N,N-dimethylformamide, dimethylsulfoxide, and acetonitrile. Preferably, the organic solvent is tetrahydrofuran, acetonitrile, methylene chloride, or ethyl acetate.

The reaction of the compound of formula (1) or a salt thereof with the magnesium salt is preferably carried out in the presence of a base. Bases usable herein include, for example, tertiary aliphatic amines such as trimethylamine, triethylamine, N,N-diisopropylethylamine, tributylamine, trioctylamine, triallylamine, dimethylbenzylamine, tetramethyl-1,3-diaminopropane, N-methylmorpholine, N-methylpyrrolidine, N-methylpiperidine, 1,8-diazabicyclo[5,4,0]undec-7-ene (DBU), and 1,5-diazabicyclo[4,3,0]non-5-ene (DBN); and nitrogen-containing heterocyclic compounds such as pyridine, 4-dimethylaminopyridine, picoline, collidine, lutidine, quinoline, and isoquinoline.

The reaction of the compound of formula (1) or a salt thereof with the magnesium salt is sometimes adversely affected by moisture and, hence, is preferably carried out in an inert gas atmosphere such as nitrogen gas or argon gas so as to avoid the inclusion of moisture in the air in the reaction system.

The compound of formula (1) according to the present invention is preferably used in a production process of a prodrug-type carbapenem antibacterial agent for oral administration, that is, a prodrug of an antibacterial carbapenem compound which can be administered orally. Therefore, in a preferred embodiment of the present invention, in the above process, the contemplated prodrug compound is a prodrug of an antibacterial carbapenem compound which can be administered orally.

A specific example of the case where the compound of formula (1) is used in a production process of a prodrug of an antibacterial carbapenem compound which can be administered orally is shown in scheme 1 which will be described later.

A compound of formula (III) with an ester group —COOR introduced therein can be produced by preparing pivaloyloxymethyl malonate as compound 2 according to the procedure in the working example which will be described later and reacting pivaloyloxymethyl malonate with a compound of formula (II) in scheme 1 as described in Reference Example 1 or 2 which will be described later (step (ii) in scheme 1). Next, a prodrug compound of formula (A) containing —COOR can be synthesized from the compound of formula (III) according to the procedure in scheme 1.

That the carbapenem derivative of formula (A) has a function as a prodrug of the carbapenem compound and the compound obtained by removing the promoiety site of the prodrug has excellent antibacterial activity in vivo is disclosed, for example, in Japanese Patent Publication No. 2666118.

The procedure of scheme 1 will be further described.

Step (i): The compound of formula (II) used in step (ii) can be produced by imidazolidating the compound of formula (I) or a salt thereof. The compound of formula (I) or a salt thereof is commercially available. The imidazolidation can be carried out by reacting the compound of formula (I) or a salt thereof with N,N-carbodiimidazole, or by reacting the compound of formula (I) or a salt thereof with a halogenated carbonic ester and imidazole in the presence of a base.

Step (iii): The compound of formula (IV) can be produced by reacting the compound of formula (III) with an azide compound. Azide compounds include, for example, sulfonyl azides such as toluenesulfonyl azide, dodecylbenzenesulfonium azide, p-carboxybenzenesulfonyl azide, and methanesulfonyl azide. This reaction is preferably carried out in the presence of a base.

Step (iv): The compound of formula (V) can be produced by reacting the compound of formula (IV) with an acid. According to this reaction, the TBS group as the protective group of hydroxyl in formula (IV) is eliminated to deprotect the compound of formula (IV). Acids usable herein include, for example, inorganic acids such as hydrochloric acid, hydrobromic acid, hydrofluoric acid, sulfuric acid, and phosphoric acid; and organic acids such as acetic acid, benzene sulfonic acid, p-toluene sulfonic acid.

Step (v): The compound of formula (VI) can be produced by subjecting the compound of formula (V) to a ring-closing reaction. This step is generally carried out in the presence of a metallic catalyst to promote the reaction. Metallic catalysts include, for example, rhodium acetate, rhodium octanoate, palladium acetate, copper sulfate, and copper bis(acetylacetonate).

Step (vi): The compound of formula (VII) can be produced by reacting the compound of formula (VI) with diphenyl chlorophosphate. This reaction is preferably carried out in the presence of a base.

Step (vii): The compound of formula (A) as a prodrug compound can be produced by reacting the compound of formula (VII) with 1-(1,3-thiazolin-2-yl)azetidin-3-thiol. This reaction is preferably carried out in the presence of a base.

Scheme 1:

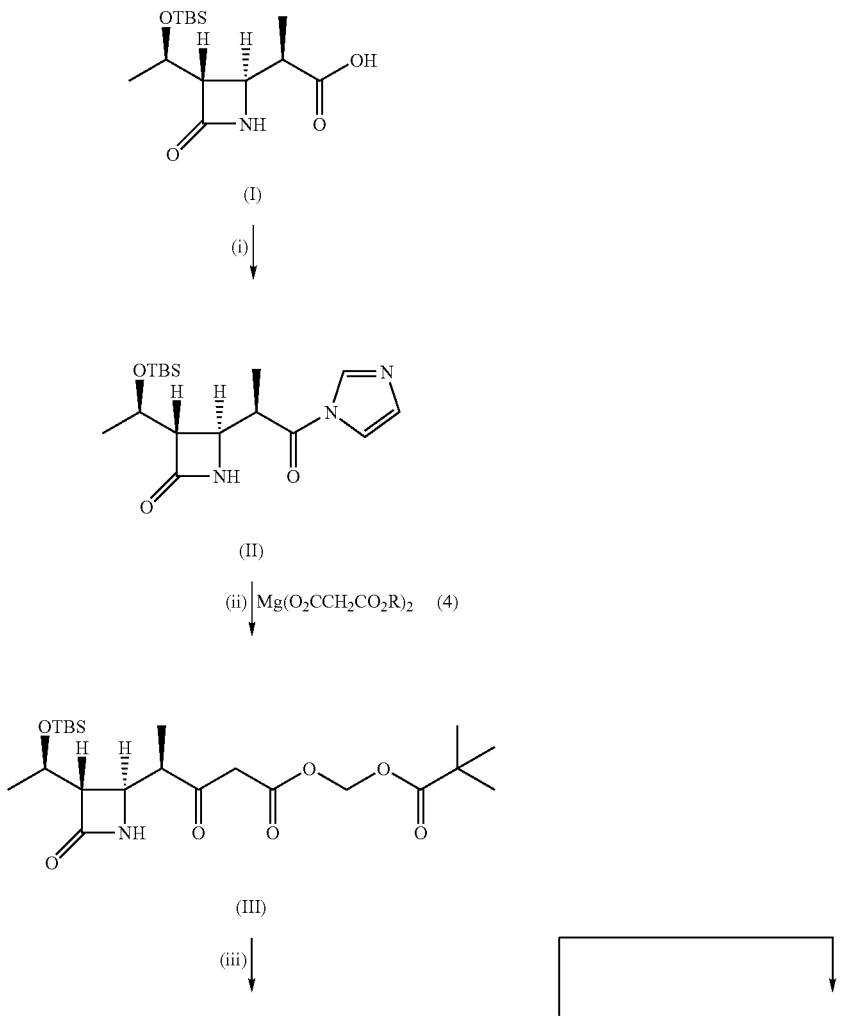

-continued

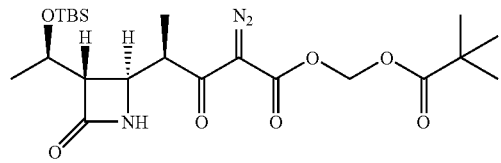

(IV)

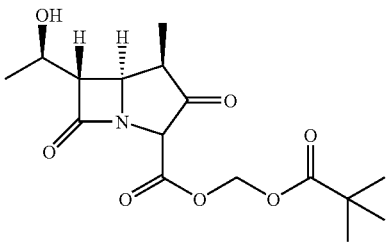

(VI)

(iv) ↓

(vi) ↓

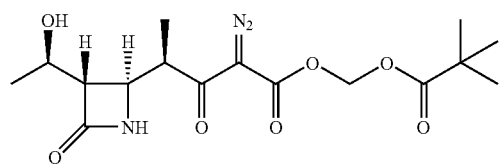

(V)

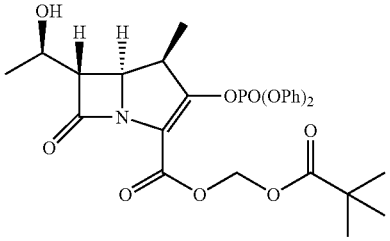

(VII)

(v)

(vii) ↓

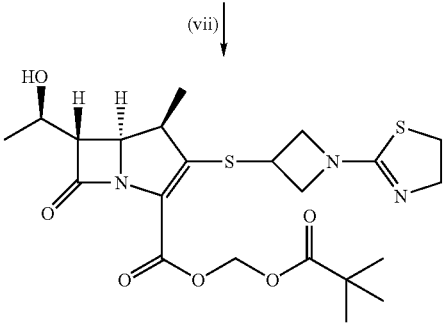

(A)

wherein TBS represents t-butyldimethylsilyl; Ph represents phenyl; and R represents pivaloyloxymethyl.

EXAMPLES

The present invention is further illustrated by the following Examples that are not intended as a limitation of the invention.

Production Examples

Compounds 1 to 18 of the present invention were produced as follows.

Compound 1: Monoacetyloxymethyl malonate

Malonic acid (4.16 g) was added to a solution (20 ml) of 1.53 g of acetyloxymethyl bromide in tetrahydrofuran to prepare a solution. N,N-Diisopropylethylamine (1.42 g) was further added to the solution, and the mixture was then stirred at an external temperature of 50° C. overnight. Ethyl acetate (30 ml) and 30 ml of 20% brine were added to the reaction solution, followed by separation. The ethyl acetate phase was washed with 30 ml of 20% brine, and the mixture was then extracted with a 5% aqueous sodium hydrogencarbonate solution. The aqueous phase was acidified with a 5 mol/l aqueous hydrochloric acid solution and was then extracted with ethyl acetate. The extract was dehydrated and dried over magnesium sulfate and was then filtered. The solvent was removed from the filtrate by distillation under the reduced pressure to give 553 mg of monoacetyloxymethyl malonate as an oil.

$^1$H-NMR (CDCl$_3$) δ: 2.14 (3H, s), 3.50 (2H, s), 5.80 (2H, s)
MS (FAB$^+$): m/z=177 (M$^+$+1)

Compound 2: Monopivaloyloxymethyl malonate

Malonic acid (5.20 g) was added to a solution (40 ml) of 2.42 g of pivaloyloxymethyl iodide in acetonitrile to prepare a solution. N,N-Diisopropylethylamine (1.42 g) was added to the solution, and the mixture was then stirred at room temperature overnight. Ethyl acetate (40 ml) and 40 ml of 20% brine were added to the reaction solution, followed by separation. The ethyl acetate phase was washed with 40 ml of 20% brine, and the mixture was then extracted with a 5% aqueous sodium hydrogencarbonate solution. The aqueous phase was acidified with a 5 mol/l aqueous hydrochloric acid solution and was then extracted with ethyl acetate. The extract was dehydrated and dried over magnesium sulfate and was then filtered. The solvent was removed from the filtrate by distillation under the reduced pressure to give 1.71 g of monopivaloyloxymethyl malonate as an oil.

$^1$H-NMR (CDCl$_3$) δ: 1.22 (9H, s), 3.49 (2H, s), 5.81 (2H, s) MS (FAB$^+$): m/z=219 (M$^+$+1)

Compound 3: Mono-2,4-dimethylbenzoyloxymethyl malonate

Sodium iodide (1.50 g) was added to a solution (20 ml) of 1.99 g of 2,4-dimethylbenzoyloxymethyl chloride in tetrahydrofuran, and the mixture was stirred at an external temperature of 50° C. for 2 hr. Malonic acid (4.16 g) and 1.42 g of N,N-diisopropylethylamine were further added thereto, and the mixture was stirred at an external temperature of 50° C. overnight. Ethyl acetate (30 ml) and 30 ml of 20% brine were added to the reaction solution, followed by separation. The ethyl acetate phase was washed with 30 ml of 20% brine and was then extracted with a 5% aqueous sodium hydrogencarbonate solution. The aqueous phase was acidified with a 5 mol/l aqueous hydrochloric acid solution, and the aqueous phase was then extracted with ethyl acetate. The extract was dehydrated and dried over magnesium sulfate and was then filtered. The solvent was removed from the filtrate by distillation under the reduced pressure to give 1.99 g of mono-2,4-dimethylbenzoyloxymethyl malonate as a yellow solid.

$^1$H-NMR (CDCl$_3$) δ: 2.36 (3H, s), 2.58 (3H, s), 3.51 (2H, s), 6.02 (2H, s), 7.04-7.07 (2H, m), 7.88 (d, J=8.7 Hz, 1H), 10.31 (1H, s) MS (FAB$^+$): m/z=267 (M$^+$+1)

Compound 4: Mono-1-(ethoxycarbonyloxy)ethyl malonate

Mono-1-(ethoxycarbonyloxy)ethyl malonate (581 mg) was prepared as a white solid in the same manner as in compound 3, except that 1.53 g of 1-(ethyloxycarbonyloxy) ethyl chloride was used instead of 1.99 g of 2,4-dimethylbenzoyloxymethyl chloride.

$^1$H-NMR (CDCl$_3$) δ: 1.33 (3H, J=7.2 Hz, t), 1.56 (3H, J=5.4 Hz, d), 3.47 (2H, s), 4.24 (2H, J=7.2 Hz, q), 6.82 (1H, J=5.4 Hz, q) MS (FAB$^+$): m/z=221 (M$^+$+1)

Compound 5: Mono-1-(isopropoxycarbonyloxy)ethyl malonate

Mono-1-(isopropoxycarbonyloxy)ethyl malonate (525 mg) was prepared as an oil in the same manner as in compound 3, except that 1.67 g of 1-(i-propoxycarbonyloxy)ethyl chloride was used instead of 1.99 g of 2,4-dimethylbenzoyloxymethyl chloride.

$^1$H-NMR (CDCl$_3$) δ: 1.31 (3H, J=6.0 Hz, d), 1.32 (3H, J=6.3 Hz, d), 1.56 (3H, J=5.4 Hz, d), 3.47 (2H, s), 4.91 (1H, m), 6.82 (1H, J=5.4 Hz, q) MS (FAB$^+$): m/z=235 (M$^+$+1)

Compound 6: Monocyclohexyloxycarbonyloxymethyl malonate

Monocyclohexyloxycarbonyloxymethyl malonate (949 mg) was prepared as a slightly yellow solid in the same manner as in compound 3, except that 1.93 g of cyclohexyloxycarbonyloxymethyl chloride was used instead of 1.99 g of 2,4-dimethylbenzoyloxymethyl chloride.

$^1$H-NMR (CDCl$_3$) δ: 1.23-1.94 (10H, m), 3.51 (2H, s), 4.68 (1H, m), 5.82 (2H, s) MS (FAB$^+$): m/z=261 (M$^+$+1)

Compound 7: Mono-1-(cyclohexyloxycarbonyloxy)ethyl malonate

Mono-1-(cyclohexyloxycarbonyloxy)ethyl malonate (1.45 g) was prepared as a slightly yellow solid in the same manner as in compound 3, except that 4.13 g of 1-(cyclohexyloxycarbonyloxy)ethyl chloride was used instead of 1.99 g of 2,4-dimethylbenzoyloxymethyl chloride.

$^1$H-NMR (CDCl$_3$) δ: 1.21-1.94 (10H, m), 1.56 (3H, d, J=5.4 Hz), 3.47 (2H, s), 4.65 (1H, m), 6.82 (1H, q, J=5.4 Hz) MS (FAB$^+$): m/z=275 (M$^+$+1)

Compound 8: Mono-1-(phenoxycarbonyloxy)ethyl malonate

Mono-1-(phenoxycarbonyloxy)ethyl malonate (302 mg) was prepared as a slightly yellow liquid in the same manner as in compound 3, except that 2.01 g of 1-(phenoxycarbonyloxy) ethyl chloride was used instead of 1.99 g of 2,4-dimethylbenzoyloxymethyl chloride.

$^1$H-NMR (CDCl$_3$) δ: 1.65 (3H, d, J=5.4 Hz), 3.50 (2H, s), 6.90 (1H, q, J=5.4 Hz), 7.18-7.42 (5H, m) MS (FAB$^+$): m/z=269 (M$^+$+1)

Compound 9: Mono-2-oxo-5-methyl-1,3-dioxolen-4-ylmethyl malonate

Mono-2-oxo-5-methyl-1,3-dioxolen-4-ylmethyl malonate (1.13 g) was prepared as a transparent liquid in the same manner as in compound 1, except that 1.93 g of 4-bromomethyl-5-methyl-1,3-dioxol-2-one was used instead of acetyloxymethyl bromide.

$^1$H-NMR (CDCl$_3$) δ: 2.19 (3H, s), 3.50 (2H, s), 4.94 (2H, s) MS (FAB$^+$): m/z=217 (M$^+$+1)

Compound 10: Mono-1-(cyclohexyloxycarbonyloxy)ethyl malonate

Sodium iodide (1.50 g) was added to a solution (20 ml) of 2.07 g of 1-(cyclohexyloxycarbonyloxy)ethyl chloride in tetrahydrofuran, and the mixture was stirred at an external temperature of 50° C. for 2 hr. Malonic acid (4.16 g) and 1.07 g of 2,6-lutidine were further added thereto, and the mixture was stirred at an external temperature of 50° C. overnight. The reaction solution was diluted with 200 ml of ethyl acetate. The dilution was then washed twice with 100 ml of half-saturated brine and was then extracted twice with 100 ml of an aqueous saturated sodium hydrogencarbonate solution. The aqueous phase was acidified with a 5 mol/l aqueous hydrochloric acid solution, and the aqueous phase was then extracted twice with 100 ml of ethyl acetate. The extract was dehydrated and dried over magnesium sulfate and was then filtered. The solvent was removed from the filtrate by distillation under the reduced pressure to give 594 mg of mono-1-(cyclohexyloxycarbonyloxy)ethyl malonate as a slightly yellow solid.

Compound 11: Mono-1-(cyclohexyloxycarbonyloxy)ethyl malonate

Sodium iodide (1.50 g) was added to a solution (20 ml) of 2.07 g of 1-(cyclohexyloxycarbonyloxy)ethyl chloride in tetrahydrofuran, and the mixture was stirred at an external temperature of 50° C. for one hr. Malonic acid (4.16 g), 1.42 g of N,N-diisopropylethylamine, and 2.28 g of benzyltriethylammonium chloride were added thereto, and the mixture was stirred at an external temperature of 50° C. for 18 hr. The reaction solution was diluted with 100 ml of ethyl acetate, and the dilution was then washed twice with 50 ml of half-saturated brine and was then extracted twice with 50 ml of aqueous saturated sodium hydrogencarbonate solution. The aqueous phase was acidified with a 5 mol/l aqueous hydrochloric acid solution, and the aqueous phase was then extracted twice with 50 ml of ethyl acetate. The extract was dehydrated and dried over magnesium sulfate and was then filtered. The solvent was removed from the filtrate by distillation under the reduced pressure to give 1.28 g of mono-1-(cyclohexyloxycarbonyloxy)ethyl malonate as a slightly yellow solid.

Compound 12: Mono-1-(2,2-dimethylpropoxy carbonyloxy)ethyl malonate

Mono-1-(2,2-dimethylpropoxycarbonyloxy)ethyl malonate (that is, mono-1-(neopentoxycarbonyloxy)ethyl malonate) (306 mg) was prepared in the same manner as in compound 3, except that 1.07 g of 1-(neopentoxycarbonyloxy)ethyl chloride was used instead of 1.99 g of 2,4-dimethylbenzoyloxymethyl chloride.
$^1$H-NMR (CDCl$_3$) δ: 0.96 (9H, s), 1.57 (3H, J=5.6 Hz, d), 3.47 (2H, s), 3.88 (2H, s), 6.82 (1H, J=5.6 Hz, q) MS (FAB$^-$): m/z=261 (M$^+$−1)

Compound 13: Mono-1-[2-(cyclohexyl)ethoxy carbonyloxy]ethyl malonate

Mono-1-[2-(cyclohexyl)ethoxycarbonyloxy]ethyl malonate (336 mg) was prepared in the same manner as in compound 3, except that 2.35 g of 1-[2-(cyclohexyl) ethoxycarbonyloxy]ethyl chloride was used instead of 1.99 g of 2,4-dimethylbenzoyloxymethyl chloride.
$^1$H-NMR (CDCl$_3$) δ: 0.88-1.72 (16H, m), 3.46 (2H, s), 4.21 (2H, J=6.8 Hz, t), 6.81 (1H, J=5.4 Hz, q) MS (FAB$^-$): m/z=301 (M$^+$−1)

Compound 14: Mono-1-(isobutoxycarbonyloxy)ethyl malonate

Mono-1-(isobutoxycarbonyloxy)ethyl malonate (331 mg) was prepared in the same manner as in compound 3, except that 1.81 g of 1-(isobutoxycarbonyloxy)ethyl chloride was used instead of 1.99 g of 2,4-dimethylbenzoyloxymethyl chloride.
$^1$H-NMR (CDCl$_3$) δ: 0.95 (6H, J=6.8 Hz, d), 1.56 (3H, J=5.4 Hz, d), 1.99 (1H, m), 3.46 (2H, s), 3.96 (2H, J=6.5 Hz, d), 6.82 (1H, J=5.4 Hz, q) MS (FAB$^-$): m/z=247 (M$^+$−1)

Compound 15: Monoisopropoxycarbonyloxymethyl malonate

Monoisopropoxycarbonyloxymethyl malonate (877 mg) was prepared in the same manner as in compound 3, except that 1.53 g of isopropoxycarbonyloxymethyl chloride was used instead of 1.99 g of 2,4-dimethylbenzoyloxymethyl chloride.
$^1$H-NMR (CDCl$_3$) δ: 1.33 (6H, J=6.3 Hz, d), 3.51 (2H, s), 4.93 (1H, m), 5.81 (2H, s) MS (FAB$^-$): m/z=219 (M$^+$−1)

Compound 16: Monoisopentoxycarbonyloxymethyl malonate

Monoisopentoxycarbonyloxymethyl malonate (765 mg) was prepared in the same manner as in compound 3, except that 1.81 g of isopentoxycarbonyloxymethyl chloride was used instead of 1.99 g of 2,4-dimethylbenzoyloxymethyl chloride.
$^1$H-NMR (CDCl$_3$) δ: 0.94 (6H, J=6.6 Hz, d), 1.58 (2H, m), 1.72 (1H, m), 3.51 (2H, s), 4.25 (2H, J=6.9 Hz, t), 5.81 (2H, s) MS (FAB$^+$): m/z=249 (M$^+$+1)

Compound 17: Monoisobutylcarbonyloxymethyl malonate

Monoisobutylcarbonyloxymethyl malonate (1.26 g) was prepared in the same manner as in compound 3, except that 1.21 g of isobutylcarbonyloxymethyl chloride was used instead of 1.99 g of 2,4-dimethylbenzoyloxymethyl chloride.
$^1$H-NMR (CDCl$_3$) δ: 0.97 (6H, J=6.6 Hz, d), 2.12 (1H, m), 2.26 (2H, J=7.3 Hz, d), 3.49 (2H, s), 5.81 (2H, s) MS (FAB$^+$): m/z=219 (M$^+$+1)

Compound 18: Mono-1-ethylpropylcarbonyloxymethyl malonate

Mono-1-ethylpropylcarbonyloxymethyl malonate (1.44 g) was prepared in the same manner as in compound 3, except that 1.65 g of ethylpropylcarbonyloxymethyl chloride was used instead of 1.99 g of 2,4-dimethylbenzoyloxymethyl chloride.
$^1$H-NMR (CDCl$_3$) δ: 0.89 (6H, J=7.3 Hz, t), 1.60 (4H, m), 2.28 (1H, m), 3.48 (2H, s), 5.83 (2H, s) MS (FAB$^+$): m/z=233 (M$^+$+1)

Production Examples of Intermediates of Prodrug Compounds using Compounds of formula (1)

Reference Example 1

Production of (3S,4R)-3-[(R)-1-(t-butyldimethylsilyloxy)ethyl]-4-[(R)-1-methyl-3-pivaloyloxymethyloxycarbonyl-2-oxopropyl]azetidin-2-one Under an argon atmosphere, 1,1'-carbonyldiimidazole (1.63 g, 10.1 mmol) was added to a solution of 3.01 g (10.0 mmol) of (3S,4S)-3-[(R)-1-(t-butyldimethylsilyloxy)ethyl]-4-[(R)-1-carboxyethyl]azetidin-2-one in tetrahydrofuran (30 mL) at room temperature, and the mixture was stirred for one hr to prepare a solution containing (3S,4S)-3-[(R)-1-(t-butyidimethylsilyloxy)ethyl]-4-[(R)-2-imidazol-1-yl-1-methyl-2-oxoethyl]azetidin-2-one.

Separately, under an argon atmosphere, magnesium bromide/diethyl ether complex (4.39 g, 17.0 mmol) was added to a solution of monopivaloyloxymethyl malonate (4.03 g, 18.5 mmol) in tetrahydrofuran (30 mL) at room temperature, and the mixture was stirred at that temperature for 30 min. Thereafter, the solution thus obtained was ice cooled. Triethylamine (2.8 mL, 20.1 mmol) was added dropwise to the solution before the temperature of the mixture was raised to room temperature. The mixture was then stirred for one hr to prepare a suspension containing a magnesium salt of monopivaloyloxymethyl malonate.

This suspension was added to the solution containing (3S, 4R)-3-[(R)-1-(t-butyldimethylsilyloxy)ethyl]-4-[(R)-2-imidazol-1-yl-1-methyl-2-oxoethyl]azetidin-2-one prepared above at room temperature, and the mixture was stirred for 3 hr. The reaction mixture was poured into a mixed liquid composed of ethyl acetate (240 mL) and 0.5 M hydrochloric acid (40 mL), and the mixture was stirred, followed by separation. The organic phase was washed with water, an aqueous saturated sodium bicarbonate solution, and saturated brine in that order and was then dried over anhydrous magnesium sulfate, and the solvent was removed by distillation under the reduced pressure. The residue was purified by column chromatography on silica gel (hexane-ethyl acetate=3:2 v/v) to give the title compound as a slightly yellow oil (3.64 g, yield 80%).

$^1$H NMR (ppm, 400 MHz, CDCl$_3$): 11.79 (s, 0.3H), 6.26 (br, 0.3H), 6.20 (br, 0.7H), 5.77 (s, 0.6H), 5.72 (ABq, J=7.8 Hz, 1.4H), 5.05 (s, 0.3H), 4.13 (m, 1H), 3.88 (dd, J=4.9, 2.4 Hz, 0.7H), 3.76 (d, J=6.6 Hz, 0.3H), 3.53 (s, 1.4H), 2.91 (m, 0.7H), 2.87 (m, 1H), 2.38 (m, J=6.8 Hz, 0.3H), 1.06-1.21 (m, 15H), 0.82 (s, 9H), 0.02 (s, 6H). MS (FAB) m/z 458 (M+H)$^+$ Reference Example 2

Anhydrous magnesium chloride powder (2.86 g, 30.0 mmol) was added to a solution of monopivaloyloxymethyl malonate (4.36 g, 20.0 mmol) in anhydrous acetonitrile under ice cooling, and the mixture was stirred for 10 min. Triethylamine (4.2 mL, 30.1 mmol) was added dropwise to the suspension under ice cooling over a period of 10 min. Next, the ice bath was removed, and the suspension was stirred for 15 min. An imidazolide solution was prepared using 3.02 g (10.0 mmol) of (3S,4S)-3-[(R)-1-(t-butyldimethylsilyloxy)ethyl]-4-[(R)-1-carboxyethyl]azetidin-2-one, 1.67 g (10.3 mmol) of N,N-carbonyldiimidazole, and acetonitrile (15 mL) in a separate vessel and was then added to the suspension, and the mixture was warmed to 30° C. and was stirred for 4.5 hr. The reaction mixture was concentrated under the reduced pressure. Ethyl acetate (80 mL) was then added to the residue, and the mixture was washed with 2 mol/L hydrochloric acid (30 mL×2), a saturated aqueous sodium bicarbonate solution (30 mL×2), and saturated brine (30 mL) in that order to give an ethyl acetate solution containing (3S,4S)-3-[(R)-1-(t-butyldimethylsilyloxy)ethyl]-4-[(R)-1-methyl-3-pivaloyloxymethyloxy-carbonyl-2-oxopropyl]azetidin-2-one (4.07 g, reaction yield 89% (yield from (3S,4S)-3-[(R)-1-(t-butyl dimethylsilyloxy)ethyl]-4-[(R)-1-carboxyethyl]azetidin-2-one)).

Application No. 2002-304630 filed Oct. 18, 2002, and Japanese Application No. 2003-50293 filed Feb. 27, 2003, the entirety of which is hereby incorporated by reference.

The invention claimed is:

1. A compound represented by formula (1) or a salt thereof:

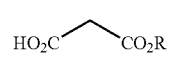

(1)

wherein R represents
- (a) C1-C6 alkylcarbonyloxy C1-C2 alkyl optionally substituted by cyclohexyl,
- (b) phenylcarbonyloxy C1-C2 alkyl in which the phenyl part is optionally substituted by C1-C4 alkyl,
- (c) C1-C6 alkoxycarbonyloxy C1-C2 alkyl optionally substituted by cyclohexyl,
- (d) phenyloxycarbonyloxy C1-C2 alkyl in which the phenyl part is optionally substituted by C1-C4 alkyl,
- (e) unsubstituted C3-C6 cycloalkyloxycarbonyloxy C1-C2 alkyl, or
- (f) unsubstituted 2-oxo-5-(C1-C4 alkyl)-1,3-dioxolen-4-ylmethyl.

2. A compound selected from the group consisting of:
monoacetyloxymethyl malonate,
monopivaloyloxymethyl malonate,
mono-2,4-dimethylbenzoyloxymethyl malonate,
mono-1-(ethoxycarbonyloxy)ethyl malonate,
mono-1-(isopropoxycarbonyloxy)ethyl malonate,
monocyclohexyloxycarbonyloxymethyl malonate,
mono-1-(cyclohexyloxycarbonyloxy)ethyl malonate,
mono-1-(phenoxycarbonyloxy)ethyl malonate,
mono-2-oxo-5-methyl-1,3-dioxolen-4-ylmethyl malonate,
mono-1-(2,2-dimethylpropoxycarbonyloxy)ethyl malonate,
mono-1-(2-cyclohexylethoxycarbonyloxy)ethyl malonate,
mono-1-(isobutoxycarbonyloxy)ethyl malonate,
monoisopropoxycarbonyloxymethyl malonate,
monoisopentoxycarbonyloxymethyl malonate,
monoisobutylcarbonyloxymethyl malonate, and
mono-1-ethylpropylcarbonyloxymethyl malonate.

* * * * *